US009517116B2

(12) United States Patent
Filtchev

(10) Patent No.: US 9,517,116 B2
(45) Date of Patent: Dec. 13, 2016

(54) METHOD FOR ARTICULATOR ADJUSTMENT AND GNATHOLOGICAL INSTRUMENTS FOR WORK UNDER THIS METHOD

(71) Applicant: F ARTICULATOR DENT, Sofia (BG)

(72) Inventor: Andon Dimitrov Filtchev, Sofia (BG)

(73) Assignee: F ARTICULATOR DENT, Sofia (BG)

( * ) Notice: Subject to any disclaimer, the term of this patent is extended or adjusted under 35 U.S.C. 154(b) by 0 days.

(21) Appl. No.: 14/414,141

(22) PCT Filed: Apr. 23, 2013

(86) PCT No.: PCT/BG2013/000018
§ 371 (c)(1),
(2) Date: Jan. 12, 2015

(87) PCT Pub. No.: WO2014/146179
PCT Pub. Date: Sep. 25, 2014

(65) Prior Publication Data
US 2015/0147726 A1 May 28, 2015

(30) Foreign Application Priority Data

Mar. 22, 2013 (BG) .......................... 111429

(51) Int. Cl.
*A61C 11/00* (2006.01)
*A61C 11/08* (2006.01)
(Continued)

(52) U.S. Cl.
CPC ........... *A61C 11/003* (2013.01); *A61C 1/0015* (2013.01); *A61C 9/0053* (2013.01); *A61C 11/006* (2013.01);
(Continued)

(58) Field of Classification Search
CPC ...... A61C 11/00; A61C 11/003; A61C 11/006; A61C 11/02; A61C 11/022; A61C 11/025; A61C 11/08; A61C 11/082; A61C 13/34; A61C 11/084; A61C 19/045; A61C 1/0015; A61C 9/0053; A61C 13/0004
(Continued)

(56) References Cited

U.S. PATENT DOCUMENTS 3,590,487 A 7/1971 Guichet
3,694,919 A 10/1972 Lee et al.
(Continued)

FOREIGN PATENT DOCUMENTS

BG 65303 B1 1/2008
EP 0170806 A1 2/1986
(Continued)

OTHER PUBLICATIONS

International Search Report for international Application No. PCT/BG2013/000018 issued on Jan. 22, 2014.

*Primary Examiner* — Nicholas Lucchesi
(74) *Attorney, Agent, or Firm* — Brown & Michaels, PC

(57) ABSTRACT

The method for articulator adjustment and gnathological instruments for work under this method find application in dental medicine and laboratory dental techniques. These and other goals of this invention are achieved with the measurement of the individual parameters of the patient's mandibular transversal hinge axis in the three planes: transversal, frontal and sagittal, including the following steps: measurement of inter-condylar distance; measurement of the distance between the condylar axis and the occlusal plane; measurement of the distance between the condylar axis and central incisors with a face-bow and bite-tray (FIGS. 1,10, 11,12); recording of values; simultaneous fixation in the articulator in minimal gathered position of the manufactured in advance two primary working models juxtaposed in
(Continued)

central position: a mandibular lower working model to the working plate of the lower articulator frame and a maxillary upper working model to the opposite working plate, which is connected in a telescopic way to the upper articulator frame (FIGS. 2,3,4,5,6,13); coincidence of the mandibular transversal hinge axis of a patient in terms of measured values of his individual parameters and the articulator transversal hinge axis (FIGS. 7,8,9,14); and closure of this articulator in an individual spread-out position.

4 Claims, 6 Drawing Sheets

(51) Int. Cl.
    *A61C 1/00*        (2006.01)
    *A61C 9/00*        (2006.01)
    *A61C 13/00*       (2006.01)
    *A61C 13/34*       (2006.01)
    *A61C 19/045*     (2006.01)

(52) U.S. Cl.
    CPC ......... *A61C 11/084* (2013.01); *A61C 13/0004* (2013.01); *A61C 13/34* (2013.01); *A61C 19/045* (2013.01)

(58) Field of Classification Search
    USPC ... 433/54, 57, 59, 60, 61, 62, 63, 68, 69, 73
    See application file for complete search history.

(56) References Cited

U.S. PATENT DOCUMENTS

| | | |
|---|---|---|
| 3,896,550 A | 7/1975 | Lee |
| 4,169,314 A | 10/1979 | Mercer et al. |
| 4,305,708 A | 12/1981 | Beu |
| 4,315,740 A | 2/1982 | Mercer et al. |
| 4,352,662 A | 10/1982 | Lee |
| 4,365,955 A | 12/1982 | Tradowsky |
| 4,371,338 A | 2/1983 | Mercer et al. |
| 4,391,589 A | 7/1983 | Monfredo et al. |
| 4,460,338 A | 7/1984 | Mercer et al. |
| RE31,716 E | 10/1984 | Lee |
| 4,504,226 A | 3/1985 | Gordon |
| 4,764,113 A | 8/1988 | Hiranuma |
| 4,773,854 A * | 9/1988 | Weber ............... A61C 11/022 433/57 |
| 5,020,993 A | 6/1991 | Levandoski |
| 5,026,282 A | 6/1991 | Koike |
| 5,064,372 A * | 11/1991 | Edwardson ............ A61C 11/08 433/60 |
| 5,073,109 A | 12/1991 | El Hadary |
| 5,076,786 A | 12/1991 | Callne |
| 5,205,737 A * | 4/1993 | White ................. A61C 11/022 433/55 |
| 5,320,528 A | 6/1994 | Alpern et al. |
| 5,385,470 A * | 1/1995 | Polz ..................... A61C 11/022 433/57 |
| 5,716,209 A | 2/1998 | Faierstain |
| 6,270,346 B1 | 8/2001 | Grabenhofer et al. |
| 6,287,113 B1 | 9/2001 | Nagata |
| 6,299,442 B1 | 10/2001 | Shiao et al. |
| 6,386,868 B1 | 5/2002 | Fujita |
| 6,558,161 B2 | 5/2003 | Nagata |
| 7,534,105 B2 * | 5/2009 | Arai ..................... A61C 11/022 433/57 |
| 8,021,149 B2 * | 9/2011 | Gutman ................ A61C 11/00 433/229 |
| 2004/0166468 A1 | 8/2004 | Hovsepian |
| 2009/0325121 A1* | 12/2009 | Ragade ................ A61C 11/022 433/57 |
| 2012/0164595 A1 | 6/2012 | Su |
| 2013/0323676 A1 | 12/2013 | Abdala Pastor |

FOREIGN PATENT DOCUMENTS

| | | |
|---|---|---|
| EP | 0362412 A1 | 4/1990 |
| EP | 0563964 A2 | 10/1993 |
| EP | 0667130 A2 | 8/1995 |
| WO | 200042941 A1 | 7/2000 |

\* cited by examiner

METHOD FOR ARTICULATOR ADJUSTMENT AND GNATHOLOGICAL INSTRUMENTS FOR WORK UNDER THIS METHOD

FIELD OF THE INVENTION

The present invention relates to dental medicine and more precisely to the method for articulator adjustment and modular gnathological instruments for work under this method. This method and modules can find application in prosthetic dental medicine and in laboratory dental techniques at the manufacture of dental prostheses by working models of the upper and/or lower jaw of patients.

BACKGROUND OF THE INVENTION

For the manufacture of convenient dental prostheses, usually, a set of instruments is used in prosthetic dental medicine and in dental technology, including the articulator as a basic apparatus and servicing dental appliances. The articulator is a mechanical instrument, which reproduces temporomandibular joints and to which maxillary and mandibular working models can be fixed, so that some or all mandibular movements can be simulated. Articulators have been systemized into four classes, as the articulators, which allow three-dimensional measurements, belong to the highest class IV. The well-known fully adjustable instruments of this type allow the orientation of working models with regard to temporomandibular joints and the imitation of mandibular movements with sufficient accuracy, but the exact imitation of each one of them cannot be expected, because articulators usually do not have freedom of movement along the three coordinate axes and do not have sufficiently big scope of change along all of them. The main requirement for articulators is they to be able to adapt to the anatomy and physiology of a patient's mouth and not vice versa. It is well-known, that the movements in joint connections are rotating and sliding ones and despite the fact, that the latter are more important ones, the accurate reproduction of all movements is of great importance, moreover, that the mobility of the two temporomandibular joints can be different.

We know an articulator with three relaying degrees of freedom and featuring rotation only in sagittal plane, described in BG 65303B, functioning together with the face-bow and a special tray. The articulator contains an upper plate for the fixation of a maxillary working model and a lower plate for the fixation of a mandibular working model. It contains also a front vertical limiter, which determines the borders of movement at bite, as well a rear frame, maintaining vertical dimension at occlusion, through an analogue of the condylar axis (mandibular transversal hinge axis) of the patient, formed by mechanical analogues of temporomandibular joints. The rear frame and the front vertical limiter connect the upper and the lower plates in a three-dimensional structure. This well-known articulator has the advantage, that it can function not only as a non-adjustable articulator, but also as an adjustable articulator, as a result of which, the number of necessary instruments is reduced and from there and broadly speaking, the consumption of materials at this process. However, the articulator has the demerits, that it does not have the capability for rotation around the three coordinate axes, as well as it cannot be fixed precisely on the axes of articulator joints, whereas mechanical condyles are vertical. This necessitates, at its adjustment, the lower working model, together with the mechanical articulator condyles, before being fixed permanently at more precise individual operations, also to be adjusted additionally, through the face-bow, which action must be repeated at every change of the models for a given patient.

The work with the well-known mechanical articulators and the connected to them face-bow and a bite-fork for adjustment, with respect to individual dental parameters and patient's correlations, is based on the orientation of working models with regard to the fixed in the sagittal plane transversal hinge axis of the adjustable articulator. This principle of articulator adjustment is stipulated in many publications about the way of work with the well-known adjustable articulators, like for example EP 0633006B1, EP 1051952, U.S. Pat. No. 4,315,740A; U.S. Pat. No. 4,460,338A, U.S. Pat. No. 5,385,470A, U.S. Pat. No. 6,287,113, U.S. Pat. No. 6,558,161, BG 65303B1 and others. This method includes the following actions: connection of the impression material of the bite-fork to the upper and/or lower patient's row of teeth; determination of a condylar axis (the transversal hinge axis of a patient) with end-pieces fixed to the face-bow; follows the connection of the face-bow to the handle of the bite-fork or vice versa-first, connection of the face-bow to the handle of the bite-fork and after that, determination of a condylar axis; the taking-out of the face-bow with the bite-fork from the patient's face; mounting of the face-bow with the bite-fork to the articulator and adjustment of the axis between the end-pieces of the face-bow till coincidence with the transversal hinge axis of the articulator; fitting of the upper or lower working model into the impression of the bite-fork; fixation of the working model to the working plate on the relevant articulator frame; dismantling of the face-bow with the bite-fork from the articulator; juxtaposition and adjustment to the fixed working model of an opposite working model; fixation of the opposite working model to the opposite articulator frame; and articulator closure.

In reality, at the application of these methods, there is a practical opportunity for relatively complete spatial orientation of the working model, which first will be fixed into the articulator. However, the demerits of these traditional methods are that, at the adjustment of working models with regard to the transversal hinge axis of the articulator, inaccuracies are possible and undesired displacements of working models one to another, whereas the fixation of working models to the relevant working plate takes place either through material accumulation, which is much more difficult to control and increases the consumption of materials of the models, or through the use of special devices (U.S. Pat. No. 4,315,740; U.S. Pat. No. 4,460,338), which complicates the kinematic chain and the very articulator, without guaranteeing the increase of accuracy and reliability. Besides that, at the repeated dismantling and change of the models in process of work over the prosthesis placement in a certain patient, the articulator adjustment becomes necessary from time to time at every change of the models, which takes time and reduces accuracy. Besides that, the positioning of the models with regard to the real position of the mandibular transversal hinge axis features reduced accuracy, whereas they are adjusted with regard to the transversal hinge axis of the articulator and in this way, there is no reproduction of the specific real position of the mandibular hinge axis of a certain patient over the dental articulator.

Another very important demerit is that at the application of well-known methods, articulator adjustment with respect to the individual dental parameters of a patient is done in a mechanical way, as the face-bow with the bite-fork (tray) is adapted to it, which complicates the whole procedure. Besides that, the connection of the face-bow to the articulator requires a complex multi-hinge connecting element, whose fixation is greatly hampered, as well as an additional supporting element to the articulator base or to the panel onto which the articulator is placed, which reduces the reliability of this connection. Additional inaccuracies and displacements are also possible at the connection of the intra-oral fork (tray) with the face-bow and they together are connected to the articulator.

We know also methods for computer virtual juxtapositions between virtual working models and a virtual articulator, which also are based on the correlations in the model presentation of the jaws in occlusion and an analogue of the condylar axis between temporomandibular joint connections. Virtual working methods include the following actions: scanning of the morphological features of teeth, of rows of teeth and/or of toothless alveolar ridges in the patient's mouth and recording of the patient's individual parameters, construction of virtual working models on their own or in occlusion, the selection of a virtual articulator of an appropriate type, coincidence of the virtual condylar axis of the virtual working models, on their own or in occlusion, with the virtual condylar axis of a virtual articulator, simulation and recording in dynamics of the movements of the mandibular working model with respect to the maxillary working model. The demerits of these methods are that they require costly and complex for work and management specialized CAD/CAM software products at modeling, as well as digital programmable milling machines for the manufacture of prostheses, which increases the service price.

At the application of these computerized methods, virtual articulators also include the upper plate for the fixation of a maxillary working model and the lower plate for the fixation of a mandibular working model. They also contain a front vertical restrictor, which delimitates the movement at the fork-bite, as well as the rear frame, maintaining vertical dimension at occlusion, through an analogue of the patient's condylar axis, formed by analogues of temporomandibular joints. The rear frame and the front vertical limiter connect the upper and the lower plates in a three-dimensional structure.

Experts are looking for ways and means for the reduction of the material consumption of working models, as well as for improving the accuracy of their positioning, with regard to the real position of the transversal hinge axis, which considerably increases accuracy and precision at the manufacture of dental prostheses. I would like also to lay emphasis on the provision of an opportunity for greater adaptability, without requirements for additional skills for work with complex software products.

SUMMARY OF THE INVENTION

The purpose of the present invention is to create a method for the adjustment of an articulator and gnathological instruments for work under this method, by help of which, accuracy and reliability at work will be improved, as well as the material consumption of working models is reduced.

These and other goals of this invention are achieved at the application of the suggested method for articulator adjustment with values from the measurement of the individual parameters of the patient's mandibular transversal hinge axis in the three planes: transversal, frontal and sagittal, including the following actions: measurement of inter-condylar distance; measurement of the distance between the condylar axis and the occlusal plane; measurement of the distance between the condylar axis and central incisors; simultaneous fixation of the manufactured in advance two primary working models juxtaposed in central position: a mandibular lower working model to the working plate of the lower articulator frame and a maxillary upper working model to the opposite working plate, which is connected in a telescopic way to the upper articulator frame; coincidence of the mandibular transversal hinge axis of a patient in terms of measured values of his individual parameters and the articulator transversal hinge axis; and closure of this articulator in an individual spread-out position.

Here, the coincidence of the mandibular transversal hinge axis of a patient with the transversal hinge axis of an articulator is realized through the telescopic relocation along the middle line of the articulator on working plates with models located in the transversal plane of this articulator; adjustment of the measured individual values: inter-condylar distance, distance between the condylar axis and the occlusal plane and distance between the condylar axis and central incisors, through three-dimensional relocation and rotation around the three coordinate axes with the fixation of location simultaneously on both mechanical joint condyles and the joint fossae of this articulator, with respect to the measured individual parameters of the mandibular transversal hinge axis of a patient.

In one variant of this method, after the action for articulator closure, the following actions are also included: subsequent opening of this articulator; dismantling of primary working models; placing and fixation of other upper and lower working model to the working plates on the relevant articulator frames, so that the middle lines of the models and of the articulator will coincide and the occlusal plane of the working models will coincide with the transversal plane of this articulator; relocation along the middle line on working plates with models in the transversal plane of an articulator; adjustment of the measured values: inter-condylar distance, the distance between the condylar axis and the occlusal plane, the distance between the condylar axis and the incisive point of central incisors, through relocation and rotation around the three coordinate axes with the fixation of location simultaneously on both mechanical joint condyles and the joint fossae of this articulator, with respect to the measured individual parameters of the mandibular transversal hinge axis of a patient; and closure of this articulator in an individual spread-out position.

In one preferred variant of this invention, the measurement of the individual parameters of the mandibular transversal hinge axis of a patient is made electronically, through scanning and recording and there is mechanical or automatic adjustment of this articulator with the measured individual values.

In another preferred variant of this method for articulator adjustment, a face-bow and the bite-tray are placed on the patient's face, by the help of which, the individual parameters of the mandibular transversal hinge axis are measured mechanically and the articulator is adjusted with the measured individual values mechanically or automatically, without adapting to it the same face-bow and the bite-tray.

BRIEF DESCRIPTION OF THE DRAWINGS

The functioning of this invention will be described in the explanations to the enclosed drawings, where on.

EXAMPLES OF PERFORMANCE

Figure 10:
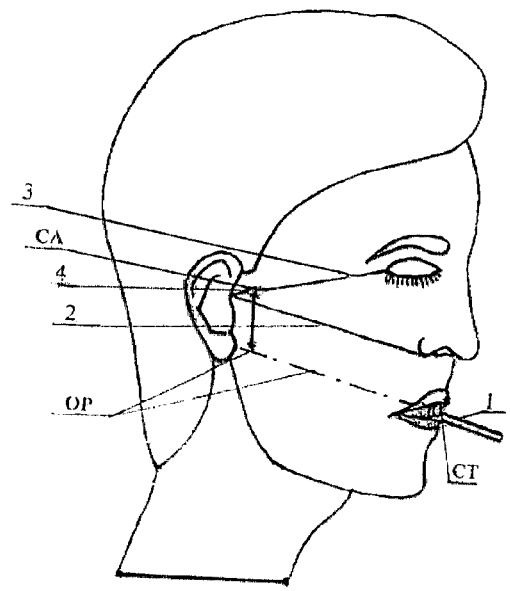
FIGS. 10, 11, 12,13 and 14 are depicted 5 basic actions of the suggested method for articulator adjustment and modular gnathological instruments for work under this method.

The present invention has been demonstrated in the enclosed drawings and visualized with examples below, which serve only for the illustration of steps:

Step 1. The positioning and fixation with impression material of a special intra-oral tray to the upper jaw for impression into the bite, at which the tray handle (1) and the occlusal plane (OP; FIG. 10/1 and OP) must be parallel to the Camper line (FIG. 10/2), which connects the middle of the ear tragus and the wing of the nose, as well as marking on the line tragus—ectocanthion (the external angle of the eye, FIG. 10/3) of a point over the skin at 13 mm in front of the tragus (FIG. 10/4), as well as marking on the tray handle of the incisive point of the upper central incisors (FIG. 10/CT).

Figure 1:
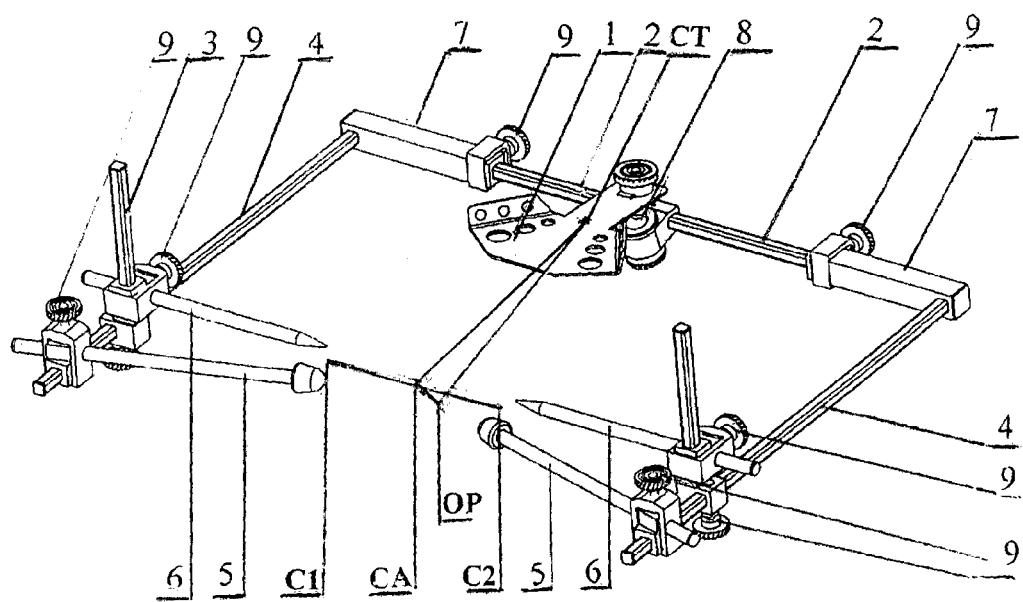
FIG. 1 a face-bow is drawn, which in the middle from above is connected in a mobile way to the intra-oral tray (1)
Figure 2:
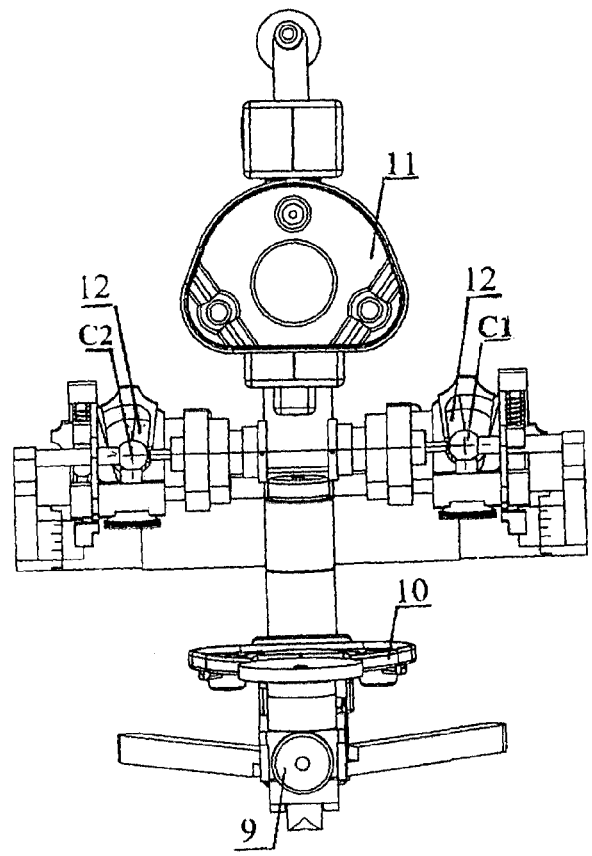
FIG. 2 an articulator is shown in an open position with a raised upper frame (11), so that you can see the joint condyles (C1 and C2) and the joint fossae (12)
Figure 11:
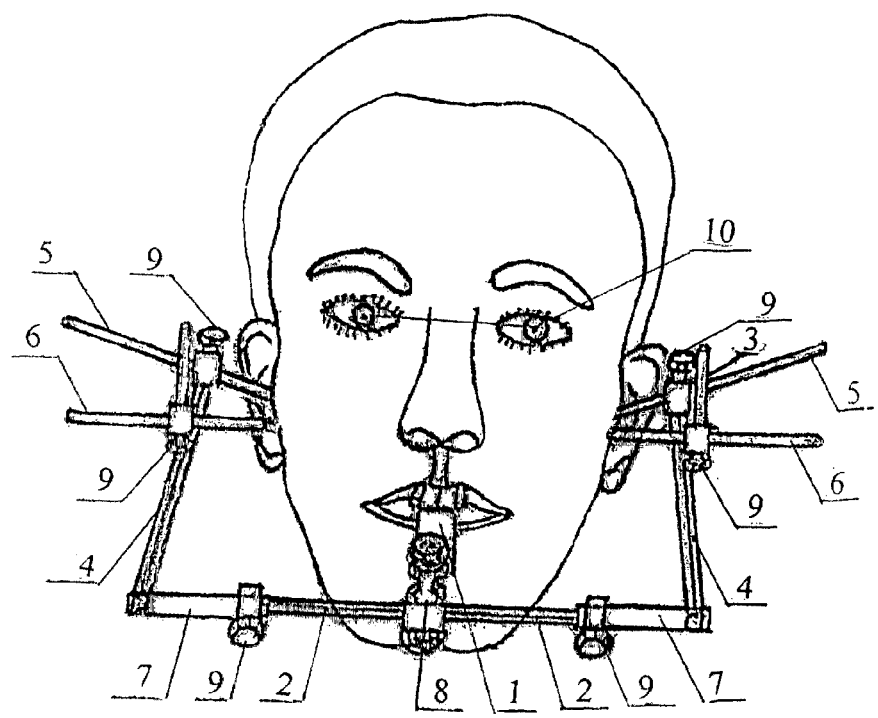

Step 2. Positioning of the face-bow (FIG. 1) to the tray handle (FIG. 1/1) at the upper jaw in a bite with the lower jaw (FIG. 11/1). This action is performed, because by means of the face-bow one can make a three-dimensional movement in the three main planes: transversal, frontal and sagittal, as well as rotation in all directions, which is due to the telescopic connection of the face-bow with the spherical joint (FIG. 1/8; FIG. 11/8). Positioning is done in such way, that: the transversal stem (shown on FIG. 1/2; FIG. 11/2) must be in collected position, parallel to the bi-pupillary line (FIG. 10/11) and its mobile connection with both corner bodies, one left and one right (FIG. 1/7, FIG. 11/7) must be fixed (FIG. 1/9; FIG. 11/9). In the other end of the two corner bodies (FIG. 1/7; FIG. 11/7), two longitudinal stalks are immovably connected, one to the left and one to the right (FIG. 1/4; FIG. 11/4), in the end of which, four sagittal stems are located in a mobile way, orientated in such way, that they are easy to place, two ear stems in the external ear hole (meatus accusticus externus), one to the left and one to the right (FIG. 1/5, FIG. 11/5) and two conical stems (FIG. 1/6; FIG. 11/6), which are located movably on the vertical stem (FIG. 1/3; FIG. 11/3) and which must be directed in a skin point, at 13 mm in front of the ear tragus (FIG. 10/4), one to the left and one to the right (FIG. 1/6; FIG. 11/6); the face-bow is fixed in such position by means of screws (FIG. 1/9 and FIG. 11/9).

Figure 12:
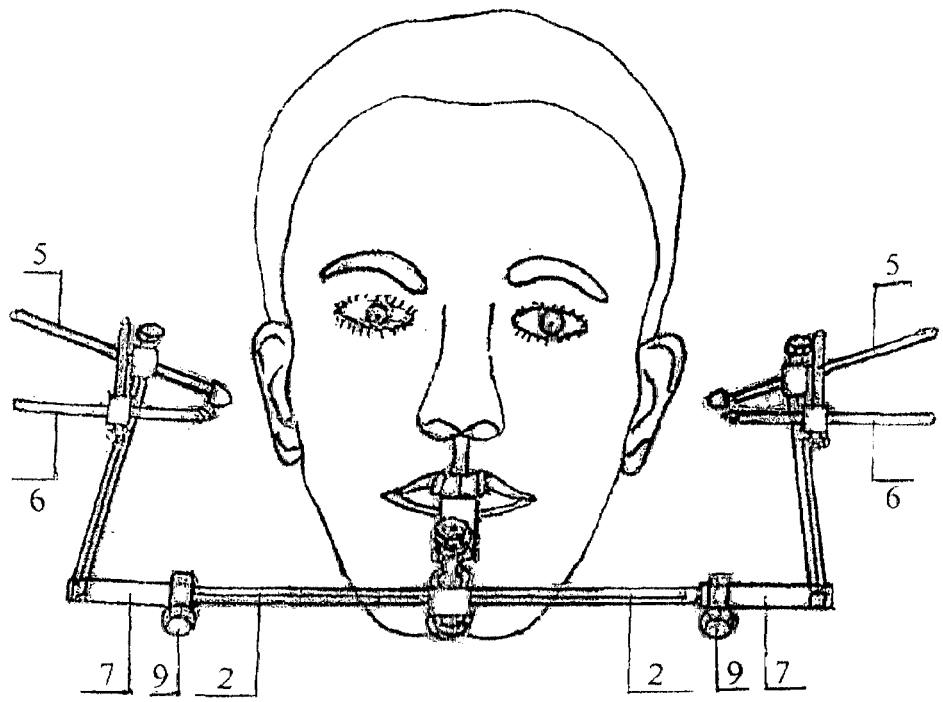

Step 3. The taking-out of the face-bow, together with the bite-tray, from the patient's face is possible, without changing the fixed distances, because the corner bodies (FIG. 1/7 and FIG. 11/7), situated in both ends of the transversal stem (FIG. 1/2 and FIG. 11/2), together with the ear stems (FIG. 11/5) and conically (FIG. 11/6) can be elongated sideways (FIG. 12/2,7), after loosening the screws (FIG. 12/9); relocation of the face-bow together with the bite-tray from the patient's face; the return of the transversal stem (FIG. 12/2,7), together with the ear stems (FIG. 12/5) and the conical stems (FIG. 12/6) in an initial gathered position (FIG. 1) and tightening of the screws (FIG. 12/9); measurement by the treating medical specialist of the values of individual parameters: distance C1/C2 (FIG. 1)-middle inter-condylar distance; CA/OP (FIG. 1) the distance between the condylar axis and the occlusal plane; CA/CT (FIG. 1) represents the distance between the condylar axis and the incisive point of the upper central incisors; the distance between the points OP and CT (FIG. 1); the dispatch of the recorded individual values to the dental technical laboratory for individual articulator adjustment.

Figure 3:
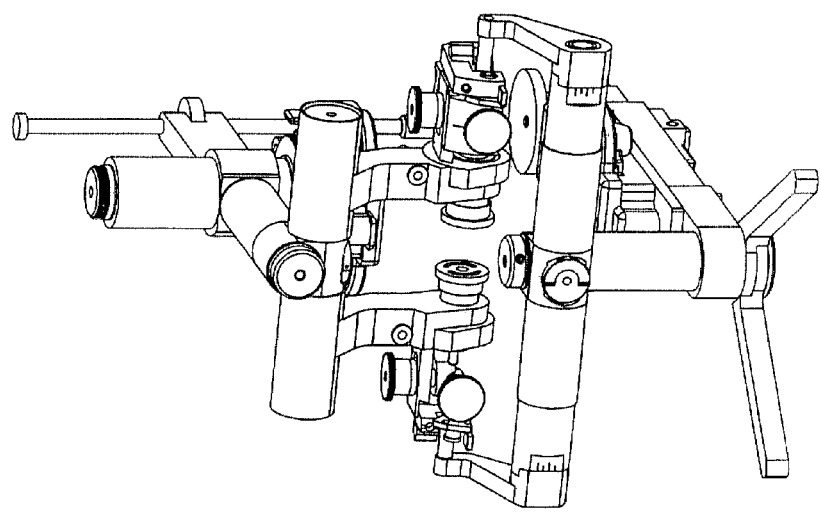
FIG. 3 an articulator is drawn viewed from behind and from aside in a compact minimal collected position.
Figure 5:
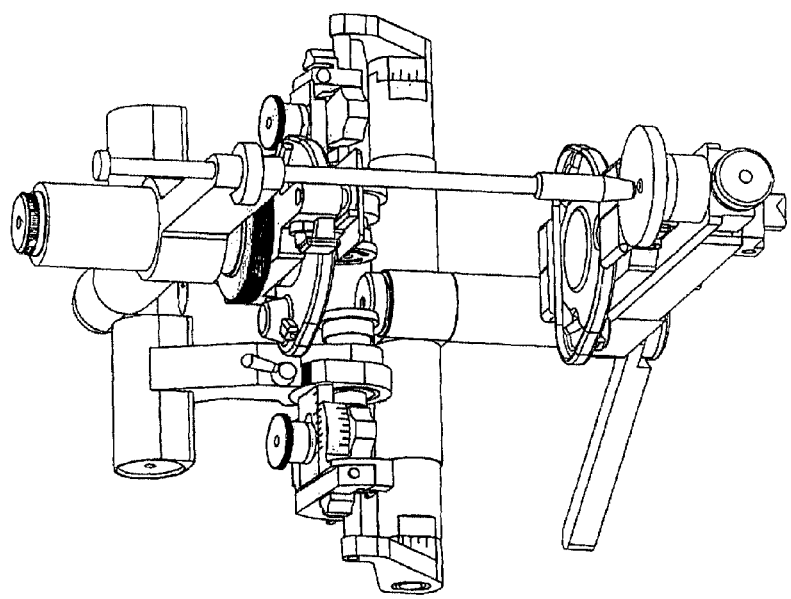
FIG. 5 the articulator from FIG. 3 is given viewed at the front and from aside in a compact minimal collected position.
Figure 13:
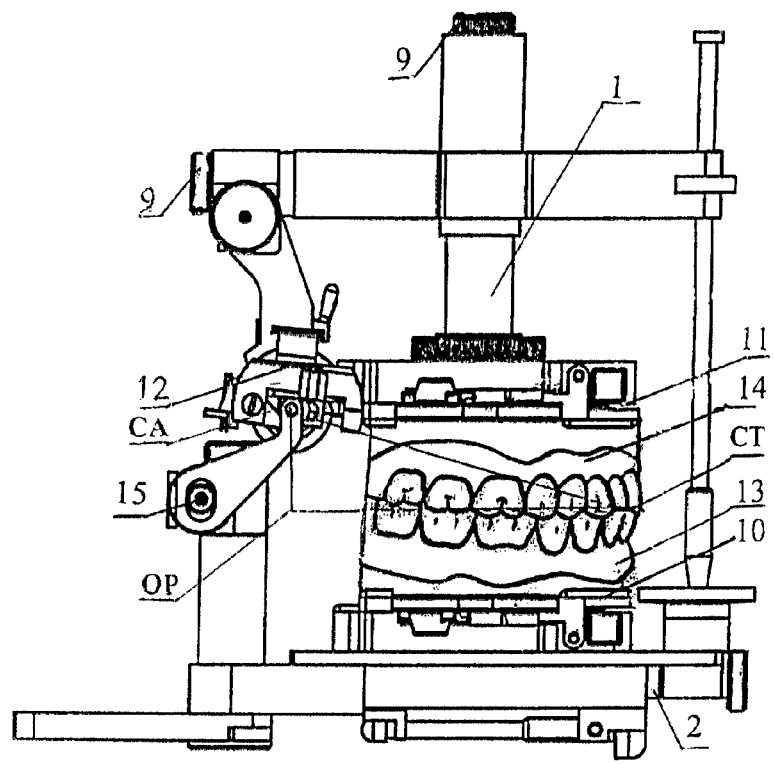

Step 4. Simultaneous fixation of the manufactured in advance two primary working models juxtaposed in central position: a mandibular lower working model (FIG. 13/13) to the working plate of the lower articulator frame (FIG. 13/10) and a maxillary upper working model (FIG. 13/14) to the opposite working plate (FIG. 13/11), which is connected in a telescopic way to the upper articulator frame (FIG. 13/1). During the fixation of working models, the mechanical articulator joint (FIG. 13/12) and the articulator are in a minimal gathered position (FIGS. 3, 5, 13).

Figure 4:
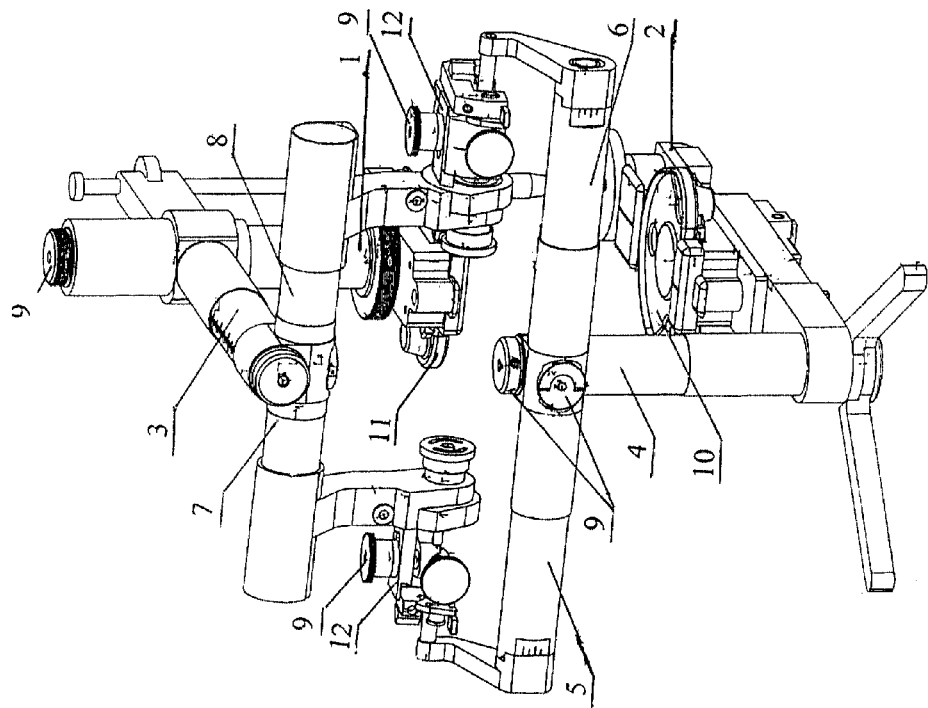
FIG. 4 the articulator from FIG. 3 is shown in a maximal spread-out position, which has been achieved through telescopic connection (FIG. 4, positions 1,2,3,4,5,6,7,8)
Figure 14:
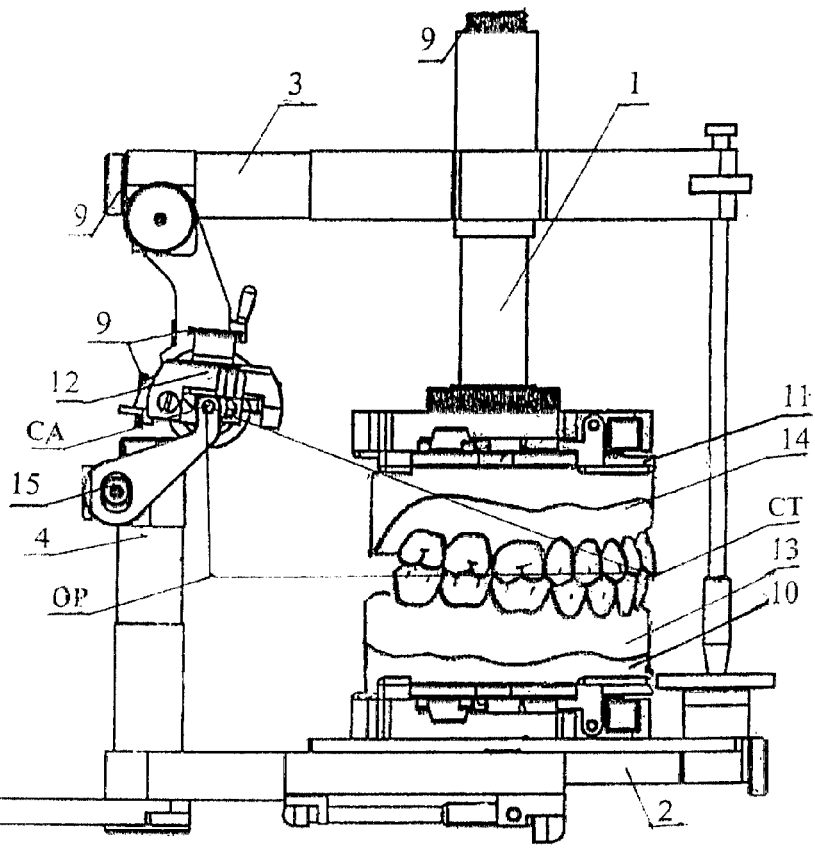

Step 5. Coincidence of the patient's mandibular transversal hinge axis in terms of measured values of individual parameters and the articulator transversal hinge axis, through telescopic relocation along the middle line on working plates with models in the transversal plane of an articulator (FIG. 13/2,4,5; FIG. 14/2,4,5) and adjustment of the measured values: inter-condylar distance C1/C2 (FIG. 1; FIG. 4); the distance between the condylar axis and the occlusal plane, CA/OP (FIG. 1; FIG. 14); the distance between the points OP and CT (FIG. 1; FIG. 14) and the distance between the condylar axis and the central incisors CA/CT (FIG. 1; FIG. 14), through three-dimensional relocation with rotation around the three coordinate axes and fixation of the newly-obtained individual location of the working models and simultaneously of the two mechanical joint condyles and the joint fossae of the articulator (FIG. 14/12,9).

Figure 6:
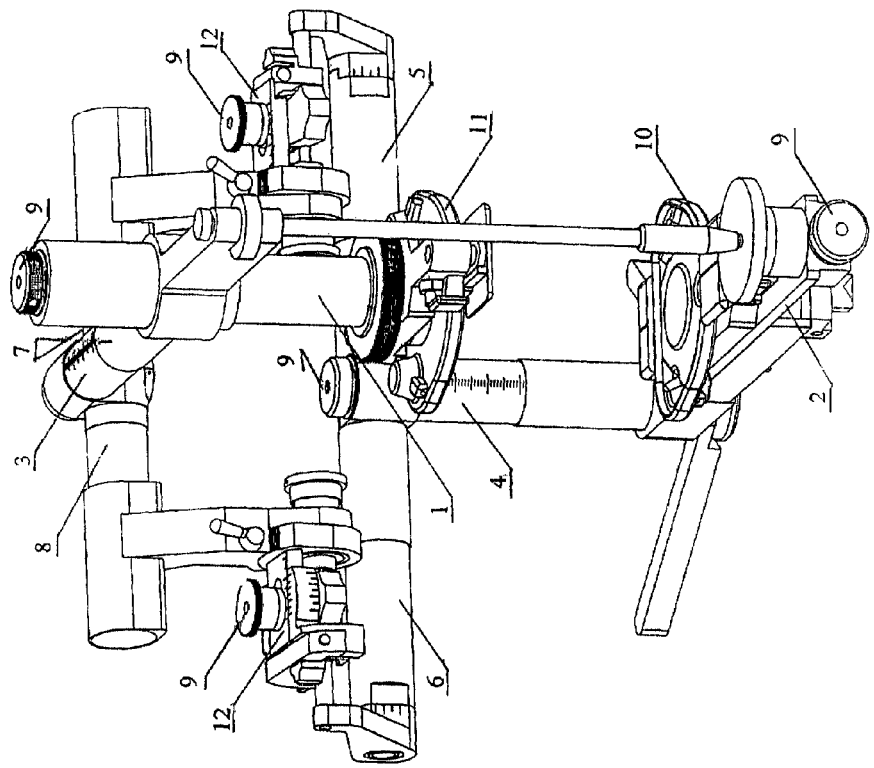
FIG. 6 the articulator from FIG. 5 is presented in a maximal spread-out position, which has been achieved through telescopic connection (FIG. 6, positions 1,2,3,4,5, 6,7,8)
Figure 7:
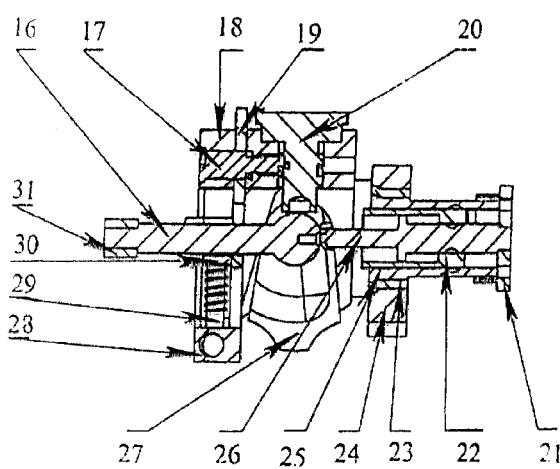
FIGS. 7, 8 and 9 the mechanical joint of the articulator from FIGS. 2, 3, 4, 5 and 6 is shown in transversal section from below (FIG. 7), in sagittal section (FIG. 8) and viewed from behind in the frontal plane (FIG. 9). The individual details of the mechanical joint are shown on FIGS. 7, 8 and 9 (positions from N 16 up to N 32), which are: a spherical joint—16; screw axis—17; cradle—18; fixator—19; special screw—20; stopper—21; bush—22; bearing bush—23; eccentric—24; hollow axis—25; floating axis—26; joint fossae—27; carrier—28; pin—29; returner—30; fork—31; nut—32.
Figure 8:
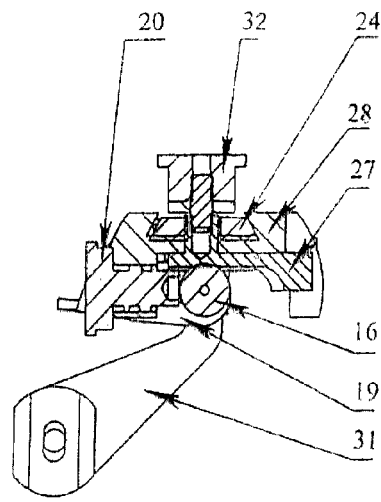
Figure 9:
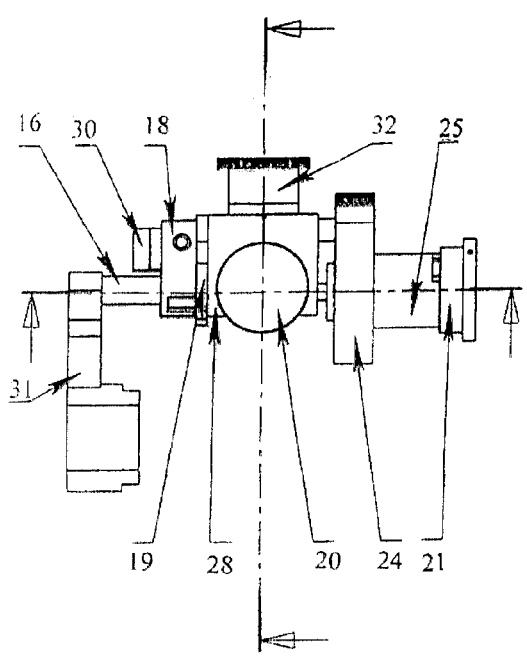

Step 6. It features the adjustment of the mechanical joint (FIG. 4/12; FIG. 6/12; FIG. 14/12 with individual values: sagittal inclination of the condyle path (protrusive condyle path); laterotrusive and mediotrusive condyle path (Bennett angle): immediate or progressive side shift; retrusive condyle path; compression or distraction of the joint heads in both joint fossae (FIG. 13/15 and FIG. 14/15) of the mechanical joints (please, see position 12 on the enclosed FIGS. 2,4,6,7,8,9,13,14). Adjustment is done through the matching of the individual details of the mechanical joint, shown on FIGS. 7, 8 and 9 (positions from 16 up to 32).

Step 7. Articulator closure in an individual spread-out position.

The above-described examples of performance and variants serve only for illustration and do not restrict the inventor's idea, which is determined by the scope of the enclosed patent claims.

BIBLIOGRAPHY

Patents

BG 65303B;
BG 65303B1;
EP 0633006B1;
EP 1051952;
U.S. Pat. No. 4,315,740A;
U.S. Pat. No. 4,460,338A;
U.S. Pat. No. 5,385,470A;
U.S. Pat. No. 6,287,113;
U.S. Pat. No. 6,558,161.

The invention claimed is:

1. A method for adjustment of an articulator for a patient, the articulator comprising an upper articulator frame having a working plate, a lower articulator frame having a working plate, and a hinge adjustably linking the upper articulator frame and the lower articulator frame, the hinge having a transversal hinge axis, two mechanical joint condyles and two joint fossae, the method comprising the steps of:

measuring individual parameters of the patient's mandibular transversal hinge axis in three planes: transversal, frontal and sagittal, the individual parameters comprising an inter-condylar distance, a distance between a condylar axis and an occlusal plane, and a distance between the condylar axis and central incisors;

fixing a manufactured in advance primary lower working model to the working plate of the lower articulator frame and a manufactured in advance primary upper working model to the working plate of the upper articulator frame;

coinciding the patient's mandibular transversal hinge axis in terms of the individual parameters and the transversal hinge axis of the hinge of the articulator; and closing the articulator in an individual spread-out position, wherein:

the step of fixing the primary upper working model and the primary lower working model before the step of coinciding the transversal hinge axis of the patient and the transversal hinge axis of the articulator, through their simultaneous placing and fixation to the working plates on the articulator frames, so that middle lines of the models and of the articulator coincide and occlusal planes of the working models are parallel to a transversal plane of the articulator;

the step of coinciding the transversal hinge axis of the patient and the transversal hinge axis of the articulator is achieved through telescopic relocation along the middle line of the articulator on the working plates with models in the transversal plane of the articulator and adjustment of measured values for the inter-condylar distance, the distance between the condylar axis and the occlusal plane, and the distance between the condylar axis and the incisive point of the patient's upper central incisors, through simultaneous three-dimensional relocation and rotation around three coordinate axes with fixation of a location of the two mechanical joint condyles and the two joint fossae of the hinge of the articulator, with regard to the measured individual parameters of the transversal hinge axis of the patient.

2. The method for articulator adjustment of claim 1, further comprising, after the step of closing the articulator, the steps of:

opening the articulator;

dismantling the primary working models;

placing and fixing other lower and upper working models to the working plates of the upper articulator frame and the lower articulator frame, so that the middle lines of the other lower and upper working models coincide with the middle lines of the working plates of the articulator and the occlusal plane of the other lower and upper working models are parallel to the transversal plane of the articulator;

relocating the other lower and upper working models fixed to the working plates of the upper articulator frame and the lower articulator frame along the middle line of the on working plates in the transversal plane of the articulator;

adjusting the measured values for the inter-condylar distance, the distance between the condylar axis and the occlusal plane, and the distance between the condylar axis and central incisors, through relocation and rotation around the three coordinate axes with the fixation of the location simultaneously of the two mechanical joint condyles and the two joint fossae of the hinge of the articulator and articulator closure in an individual spread-out position.

3. The method for articulator adjustment of claim 1, in which the measurement of the individual parameters of the transversal mandibular hinge axis of a patient is made electronically, through scanning and recording.

4. The method for articulator adjustment of claim 1, in which the measurement of the individual parameters of the patient's transversal mandibular hinge axis is made mechanically, through a face-bow and a bite-tray or bite-fork.

* * * * *